US00PP24778P3

(12) United States Plant Patent
Potgieter

(10) Patent No.: US PP24,778 P3
(45) Date of Patent: Aug. 19, 2014

(54) ORANGE TREE NAMED 'KIRKWOOD RED'

(50) Latin Name: *Citrus sinensis*
Varietal Denomination: Kirkwood Red

(75) Inventor: André Potgieter, Kirkwood (ZA)

(73) Assignee: Kirkwood Red Trust, Kirkwood (ZA)

( * ) Notice: Subject to any disclaimer, the term of this patent is extended or adjusted under 35 U.S.C. 154(b) by 13 days.

(21) Appl. No.: 13/385,922

(22) Filed: Mar. 13, 2012

(65) Prior Publication Data

US 2013/0247256 P1 Sep. 19, 2013

(51) Int. Cl.
*A01H 5/00* (2006.01)

(52) U.S. Cl.
USPC ..... Plt./202; Plt./201

(58) Field of Classification Search
USPC ..... Plt./201, 202
See application file for complete search history.

(56) References Cited

PUBLICATIONS

PLUTO: Plant Variety Database, citation for Orange plant named 'Kirkwood Red' (ES PBR 20074754, filed Nov. 28, 2007, and denomination published Dec. 1, 2008). (https://www3.wipo.int/pluto/user/en/index.jsp, Jul. 17, 2013).*
PLUTO: Plant Variety Database, citation for Orange plant named 'Kirkwood Red' (ES, NLI 20070368, filed Nov. 28, 2007, and denomination published Dec. 1, 2008). (https://www3.wipo.int/pluto/user/en/index.jsp, Jul. 17, 2013).*
PLUTO: Plant Variety Database, citation for Orange plant named 'Kirkwood Red' (ZA PBR PT 4924, filed Feb. 5, 2007 and denomination approved Oct. 10, 2008). (https://www3.wipo.int/pluto/user/en/index.jst, Jul. 17, 2013).*
PLUTO: Plant Variety Database, citation for Orange plant named 'Kirkwood Red' (QZ PBR 20102119, filed Oct. 8, 2010 and application/denomination published Dec. 15, 2010). (https://www3.wipo.int/pluto/user/en/index.jsp, Jul. 7, 2013.*

* cited by examiner

*Primary Examiner* — June Hwu
*Assistant Examiner* — Louanne Krawczewicz Myer
(74) *Attorney, Agent, or Firm* — Michelle Bos

(57) ABSTRACT

A new and distinct variety of sweet orange tree (*Citrus sinensis*) named 'Kirkwood Red'. 'Kirkwood Red' is notable for its fruit, which has an attractive external blush, intense orange-red flesh, and exceptional taste.

5 Drawing Sheets

Genus and species: *Citrus sinensis.*
Variety denomination: 'Kirkwood Red'.

CROSS-REFERENCE TO RELATED APPLICATIONS

None

BACKGROUND AND SUMMARY OF THE VARIETY

The new orange tree 'Kirkwood Red' originated as a whole tree mutation of a 'Palmer' navel orange tree (not patented). The whole tree mutation was discovered in 1992 in a commercial orchard of 'Palmer' navel trees grown at Kirkwood, South Africa, and was distinguished by its external blush, intense orange-red flesh, and excellent flavor. Information as to which of the two rootstocks, 'Swingle' citrumelo and Cairns rough lemon rootstocks (not patented), the original 'Kirkwood Red' tree was growing on is not available. Asexual propagation by budding was carried out at Kirkwood, South Africa, to determine whether the desirable characteristics of the mutation would carry through to asexually propagated progeny. It has been found that all distinguishing characteristics of the variety are reproduced through asexual propagation, and remain stable through successive generations.

'Kirkwood Red' is a new and distinct orange tree notable for its fruit, which is distinguished by its external blush, intense orange-red flesh, and exceptional flavor. The 'Kirkwood Red' tree is distinguished by red pigmentation present in vascular bundles of the leaves and the fruit stem.

BRIEF DESCRIPTION OF THE PHOTOGRAPHS

Figure 1:
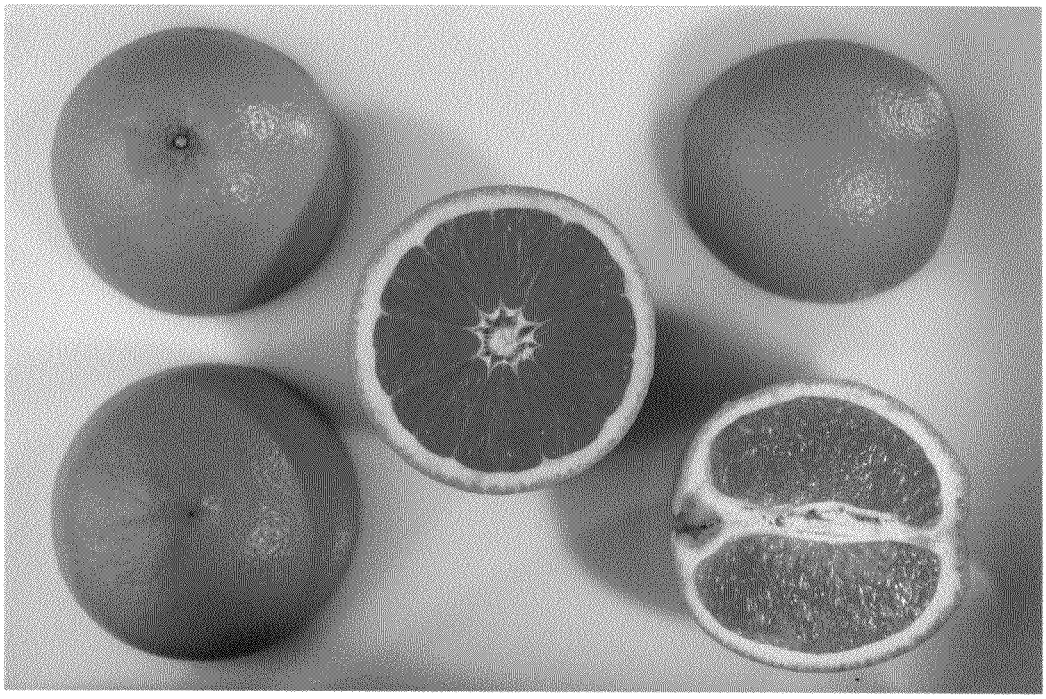
FIG. 1 shows whole and sectioned fruit of the 'Kirkwood Red' variety.
Figure 2:
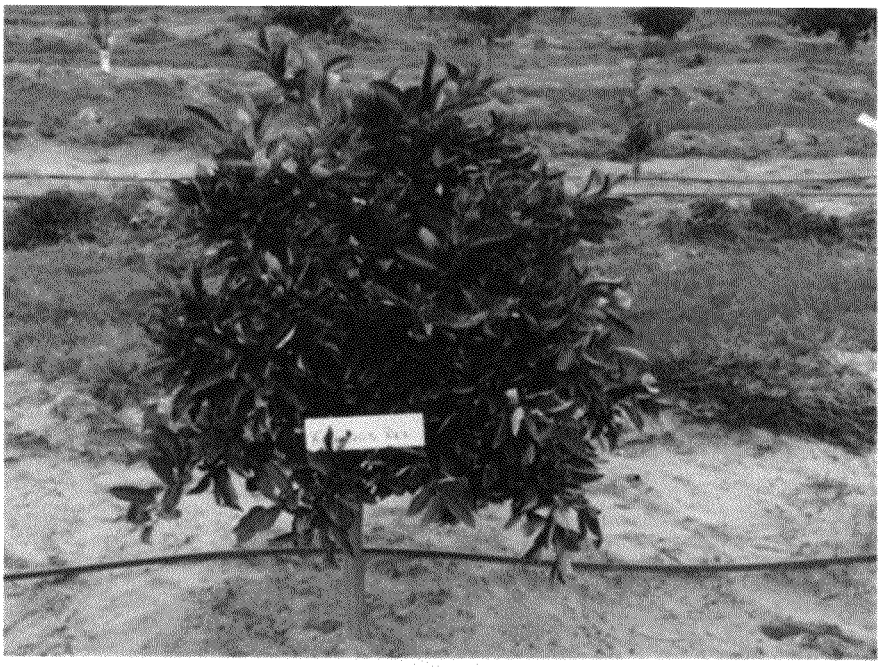
FIG. 2 shows a 'Kirkwood Red' tree on 'Carrizo' citrange rootstock (not patented)
Figure 3:
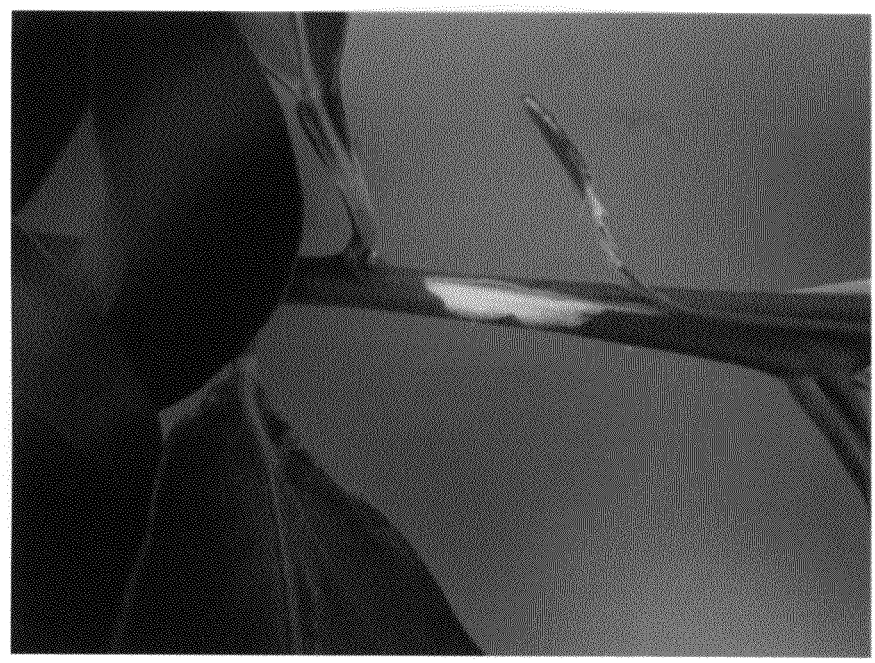
FIG. 3 shows a branch and leaves of the 'Kirkwood Red' variety.
Figure 4:
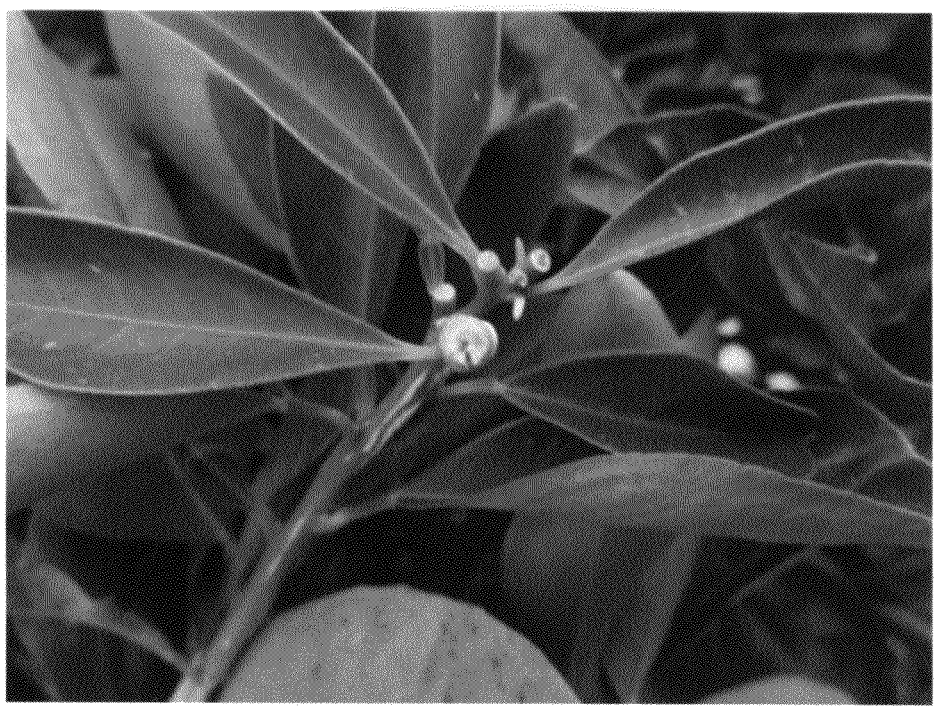
FIG. 4 shows the red pigmentation on the stalk end of the 'Kirkwood Red' variety.
Figure 5:
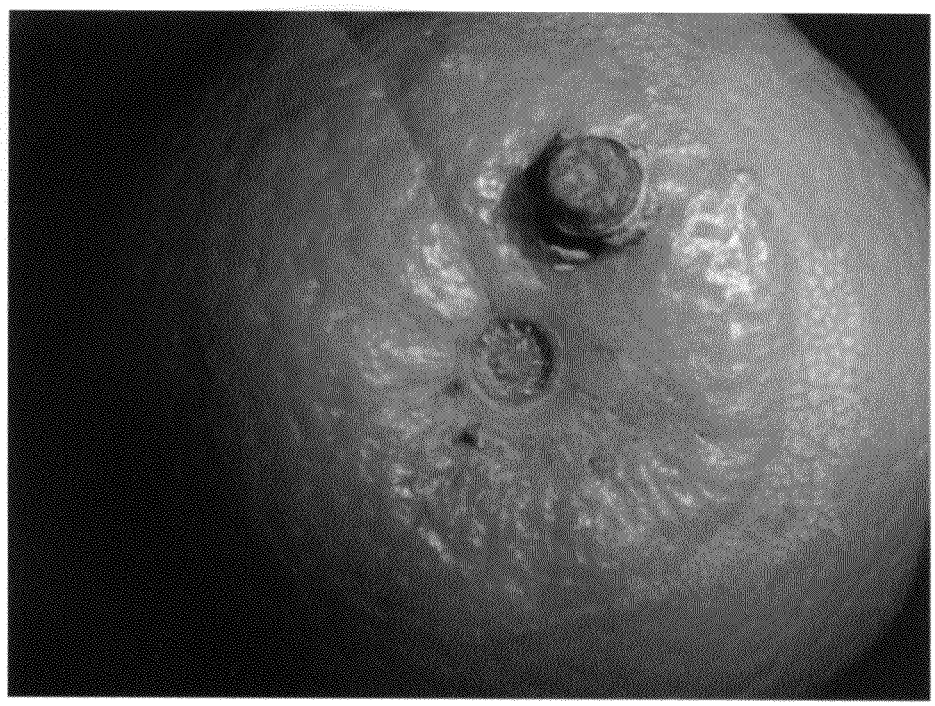
FIG. 5 shows the red pigmentation on the calyx and fruit of the 'Kirkwood Red' variety.

The colors of the claimed variety may vary with lighting conditions. Color characteristics of the variety should therefore be determined with reference to the observations described herein, rather than from these illustrations alone.

DETAILED BOTANICAL DESCRIPTION

The following detailed botanical description is based on observations of three to four-year-old 'Kirkwood Red' trees grown on 'Carrizo' citrange rootstock. Observations were recorded and photographs taken during the 2010 and 2012 growing seasons at Kirkwood, South Africa. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to The Royal Horticultural Society Colour Chart (2007).

Tree:

*Vigor*.—Comparable to 'Washington' navel (not patented).
*Density of canopy*.—Compact.
*Habit*.—Comparable to 'Washington' navel.
*Height*.—1.5 meters.
*Spread*.—1.7 meters.
*Trunk diameter*.—43 mm (30 cm above the graft).
*Bark color*.—Brown N200C.
*Bark texture*.—Smooth.
*Tendency to alternate bearing*.—None.
*Winter hardiness*.—Slightly more sensitive than non-pigmented navel varieties; similar to other red pigmented varieties.

Branches:

*Length*.—250 mm.
*Diameter*.—11 mm.
*Crotch angle*.—45° maximum.
*Color*.—Green 136C with Red 50D vascular bundle.
*Bark texture*.—Smooth.
*Thorns*.—Present on some branches, generally close to trunk and vigorous branches.
*Thorn length*.—10 mm.
*Current year shoot length*.—120 to 200 mm (latest flush).
*Current year shoot color*.—Light yellow green 150B.

Flowers:

*Bud shape*.—Elongated.
*Bud length*.—12.6 mm.
*Bud diameter*.—7.7 mm.
*Bud color*.—Green 134A.
*Quantity of blossoms per cluster*.—Up to 8.
*Blossom diameter*.—44 mm (open to ends of petals).
*Blossom depth*.—22 mm base of sepal to top of petal.
*Pollen*.—Abundant; infertile. Fruit is set parthenocarpically.
*Sepal length*.—4.9 mm.
*Sepal width*.—4.9 mm.
*Sepal shape*.—Acuminate.
*Sepal margin*.—Entire.
*Sepal color*.—Upper surface — Yellow 8A.
*Sepal color*.—Lower surface — Yellow 8A.
*Quantity of petals per flower*.—4 to 6, generally 5.
*Petal shape*.—Stellate.
*Petal apex*.—Acute.
*Petal margin*.—Entire (smooth).
*Petal length*.—21 mm.
*Petal width*.—6.5 mm.
*Petal color*.—Upper surface — White NN155D.
*Petal color*.—Lower surface — White NN155D with yellow dots.
*Date of first bloom*.—12 October.
*Date of full bloom*.—15 October.
*Date of first fruitlet fall*.—Around 21 November.
*Pedicel length*.—6.0 mm.
*Pedicel diameter*.—1.7 mm.
*Pedicel color*.—Cream to light green.
*Pistil quantity per flower*.—One.
*Pistil length*.—13.5 mm.
*Pistil color*.—Light green, yellow/cream.
*Anther quantity per flower*.—24.
*Anther length*.—1.48 mm.
*Anther color*.—Yellow 10B.
*Stigma quantity per flower*.—One.
*Stigma length*.—1.97 mm.
*Stigma color*.—Yellow green 150D.
*Style quantity per flower*.—One.
*Style length*.—6.97 mm.
*Style color*.—Yellow green 150C.
*Ovary quantity per flower*.—One.
*Ovary length*.—3.30 mm.
*Ovary diameter*.—4.56 mm.
*Ovary color*.—Yellow green 150A.

Leaves (from twigs behind latest flush):

*Length*.—70 mm.
*Width*.—32 mm.
*Length/width ratio*.—1:2.2.
*Blade margin*.—Entire to very slightly undulate.
*Blade shape*.—Elliptic, involute.
*Apex shape*.—Acute, emargination at tip.
*Base shape*.—Cuneate.
*Color*.—Upper surface — Green 136B.
*Color*.—Lower surface — Green 136C.
*Petiole length*.—12 mm.
*Petiole diameter*.—1.8 mm.
*Petiole color*.—Yellow Green 145A; vascular bundles are red 50C.
*Leaf texture*.—Smooth.
*Wings*.—Present.
*Wing width*.—3 mm.

Fruit:

*Quantity per cluster*.—2 to 3.
*Axial diameter*.—73 to 81 mm.
*Weight*.—220 g.
*General shape in profile*.—Round to slightly oval.
*Navel*.—Small navel end, sometimes closed.
*Rind color*.—Orange N25D, with orange 25A to orange-red 30A blush overcolor.
*Rind thickness*.—6 mm.
*Rind texture*.—Medium smooth to smooth; weak to medium strong gloss.
*Ease of peeling*.—Good peelability.
*Albedo*.—White to light yellow with some pink staining.
*Albedo thickness*.—3 to 4 mm.
*Toughness of segment membrane*.—Medium.
*Flesh color*.—Orange-red N30A.
*Juice sac color*.—Orange-red N32C.
*Juice sac length*.—8 mm.
*Juice sac shape*.—Elongated.
*Juice soluble solids* (*brix*).—10.7° to 11.5°.
*Percent juice*.—50% to 55%.
*Percent solids*.—10% to 13%.
*Quantity of segments per fruit*.—Generally 9 to 11.
*Seeds*.—None.
*Tendency to split*.—Very low.
*Relative harvest maturity*.—Mid-season.
*Harvest window*.—June (3 to 4 weeks).
*Fruit holding ability past maturity*.—About 6 weeks from optimum maturity.
*Harvest yield*.—38.9 kg/tree (4 year old topworks).
*Market use*.—Fresh.

The invention claimed is:

1. A new and distinct variety of orange tree, substantially as illustrated and described herein.

* * * * *